(12) United States Patent
Francis

(10) Patent No.: US 6,443,928 B1
(45) Date of Patent: Sep. 3, 2002

(54) VEIN SCOPE AND INJECTION SYSTEM

(76) Inventor: Raymond Francis, 3454 W. 123rd St., Cleveland, OH (US) 44111

( * ) Notice: Subject to any disclaimer, the term of this patent is extended or adjusted under 35 U.S.C. 154(b) by 0 days.

(21) Appl. No.: 09/823,415

(22) Filed: Apr. 2, 2001

(51) Int. Cl.[7] .................................................. A61M 5/00
(52) U.S. Cl. ...................... 604/116; 604/115; 604/117; 604/239; 604/240; 604/272
(58) Field of Search .................................. 604/115, 116, 604/117, 239, 240, 272; 606/130, 184, 185

(56) References Cited

U.S. PATENT DOCUMENTS 3,167,072 A * 1/1965 Stone et al. ................. 604/116
4,403,987 A * 9/1983 Gottinger .................... 604/115
5,147,372 A * 9/1992 Nymark et al. ............. 604/116
6,283,942 B1 * 9/2001 Staehlin et al. ............. 604/116

* cited by examiner

Primary Examiner—Robin O. Evans

(57) ABSTRACT

A vein scope comprising a monitor assembly that includes an image viewing surface and an image receiving surface. The monitor assembly is formed with a first thickness. A support assembly includes a bracket portion and an arm receiving portion. The bracket portion has a central opening forming an enclosure for the receipt and secure containment of the monitor assembly. A needle handling assembly includes spaced parallel guide rails coupled to the bracket portion. The needle handling assembly also includes a slide member with laterally spaced apertures for being slidably received on the rails and with a central aperture.

6 Claims, 3 Drawing Sheets

VEIN SCOPE AND INJECTION SYSTEM

BACKGROUND OF THE INVENTION

1. Field of the Invention

The present invention relates to a vein scope and injection system and for safely and efficiently locating veins to thereby provide precise venous access.

2. Description of the Prior Art

The use of medical devices of known designs and configurations is known in the prior art. More specifically, medical devices of known designs and configurations previously devised and utilized for the purpose of increasing the safety and efficiency are known to consist basically of familiar, expected, and obvious structural configurations, notwithstanding the myriad of designs encompassed by the crowded prior art which has been developed for the fulfillment of countless objectives and requirements.

By way of example, United States Patent Number 4,613,328 to Boyd discloses a biomedical injector apparatus. U.S. Pat. No. 5,137,518 to Mersch discloses an instantaneous vein entry indicator for intravenous needle. Lastly, U.S. Pat. No. 5,030,207 to Mersch et al discloses an instantaneous vein entry indicator for intravenous needle.

While these devices fulfill their respective, particular objectives and requirements, the aforementioned patents do not describe a vein scope and injection system that allows for the safe and efficient locating of veins to thereby provide precise venous access.

In this respect, the vein scope and injection system according to the present invention substantially departs from the conventional concepts and designs of the prior art, and in doing so provides an apparatus primarily developed for the purpose of safely and efficiently locating veins to thereby provide precise venous access.

Therefore, it can be appreciated that there exists a continuing need for a new and improved vein scope and injection system which can be used for safely and efficiently locating veins to thereby provide precise venous access. In this regard, the present invention substantially fulfills this need.

SUMMARY OF THE INVENTION

In view of the foregoing disadvantages inherent in medical devices of known designs and configurations now present in the prior art, the present invention provides an improved vein scope and injection system. As such, the general purpose of the present invention, which will be described subsequently in greater detail, is to provide a new and improved vein scope and injection system which has all the advantages of the prior art and none of the disadvantages.

To attain this, the present invention essentially comprises a monitor assembly, a support assembly and a needle handling assembly. The monitor assembly includes an image viewing surface formed as a screen in an upper plane. The monitor assembly also includes an image receiving surface formed as a camera in a lower plane parallel with and beneath the upper plane. The monitor assembly also includes electronic components capable of producing an enlarged image upon the viewing screen of an area beneath the camera. The viewing screen is in a rectangular configuration with an upper edge and a lower edge and two parallel sided edges there between. The monitor assembly is formed with a first thickness. A support assembly is next provided. The support assembly includes a bracket portion and an arm receiving portion. The bracket portion is in a rectangular configuration with an upper edge and a lower edge and two parallel side edges there between to thereby form an upper surface and a lower surface. The bracket portion has a central opening located centrally with respect to the screen. The bracket and opening forms an enclosure for the receipt and secure containment of the monitor assembly within the opening. The bracket portion further has a plurality of axles coupled horizontally adjacent to the image receiving surface. The axles have a first end and a second end with the first end being coupled to the bracket portion and the second end being coupled to a roller. These rollers have a central aperture to receive the axle. The support assembly has a second thickness which is greater than the first thickness to thereby form a chamber between the edges of the bracket portion and beneath the camera. The arm receiving portion is of a generally U-shaped trough having an interior surface, a pair vertical side walls and a generally semicircular base region, thereby defining a region to receive an arm. The vertical side walls each have an angularly oriented track wherein a recess is nearly covered by an upper lip and lower lip. Together the roller and axle combination fit within the horizontal track of the arm receiver to allow the placement of the arm of a patient in a plane generally parallel with the plane of the camera. The band has exterior edges. Next provided is a needle handling assembly. The needle handling assembly includes spaced parallel guide rails coupled to the bracket portion adjacent to the lower face and extending away from the bracket portion. The needle handling assembly also includes a slide member with laterally spaced apertures for being slidably received on the rails and with a central aperture. Lastly, a syringe is removably positioned within the central aperture of the slide member. The syringe has a needle extending into the chamber so that the tip of the needle is located within the chamber to allow the movement of the syringe and needle and slide member along the rails for advancement of the needle toward and into a vein during the enlarged viewing of the needle and an appropriate vein of a patient. In this manner precise viewing and venous access is facilitated during operation and use.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved vein scope and injection system which has all of the advantages of the prior art medical devices of known designs and configurations and none of the disadvantages.

It is another object of the present invention to provide a new and improved vein scope and injection system which may be easily and efficiently manufactured and marketed.

It is further object of the present invention to provide a new and improved vein scope and injection system which is of durable and reliable constructions.

An even further object of the present invention is to provide a new and improved vein scope and injection system which is susceptible of a low cost of manufacture with regard to both materials and labor, and which accordingly is then susceptible of low prices of sale to the consuming public, thereby making such vein scope and injection system economically available to the buying public.

Even still another object of the present invention is to provide a vein scope and injection system for safely and efficiently locating veins to thereby provide precise venous access.

Lastly, it is an object of the present invention to provide a new and improved vein scope comprising a monitor assembly that includes an image viewing surface and an image receiving surface. The monitor assembly is formed with a first thickness. A support assembly includes a bracket portion and an arm receiving portion. The bracket portion has a central opening forming an enclosure for the receipt and secure containment of the monitor assembly. A needle handling assembly includes spaced parallel guide rails coupled to the bracket portion. The needle handling assembly also includes a slide member with laterally spaced apertures for being slidably received on the rails and with a central aperture.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
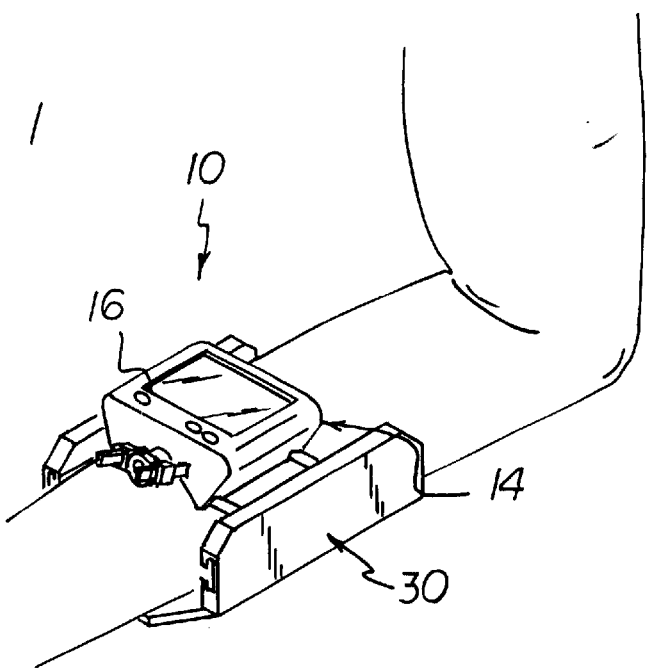
FIG. 1 is a perspective illustration of the vein scope and injection system constructed in accordance with the principles of the present invention
Figure 2:
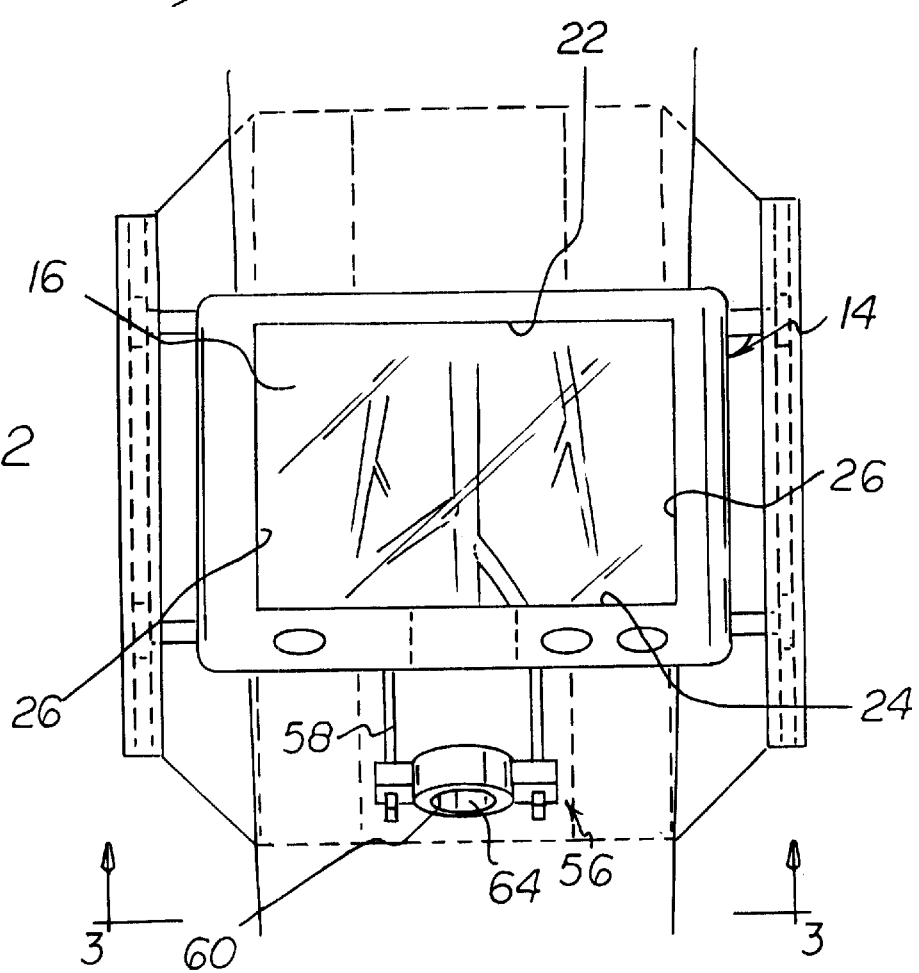
FIG. 2 is an enlarged plan view of the system shown in FIG. 1.
Figure 3:
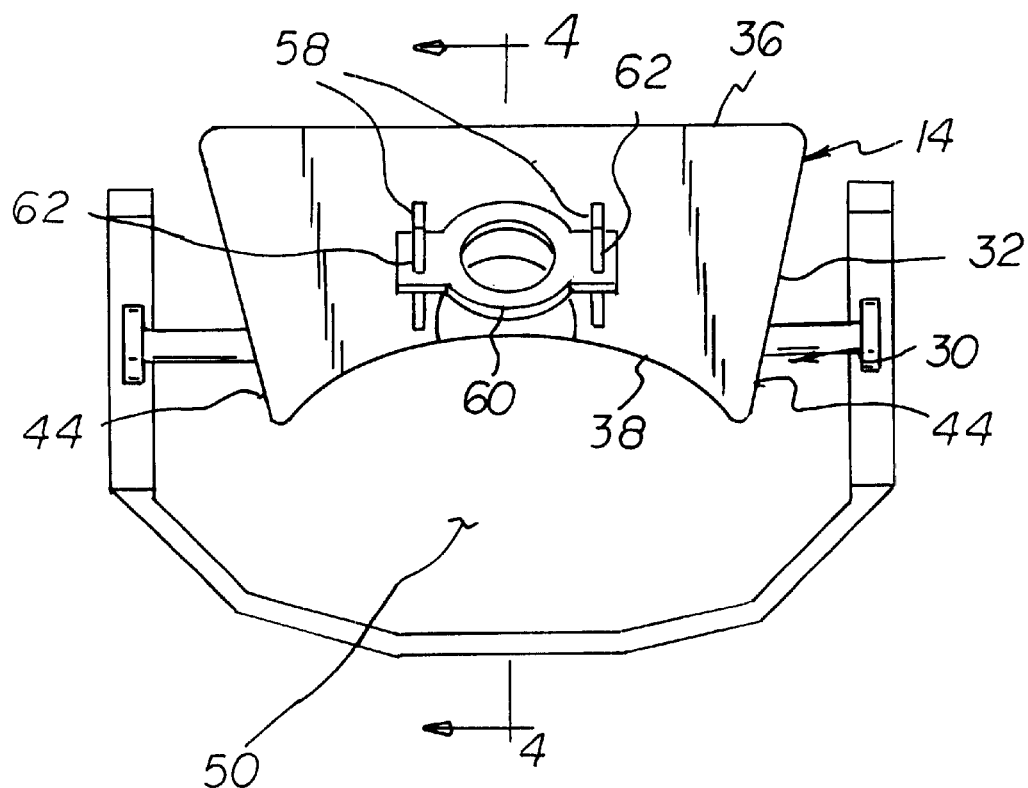
FIG. 3 is a side elevational view of taken along line 3—3 of FIG. 2.
Figure 4:
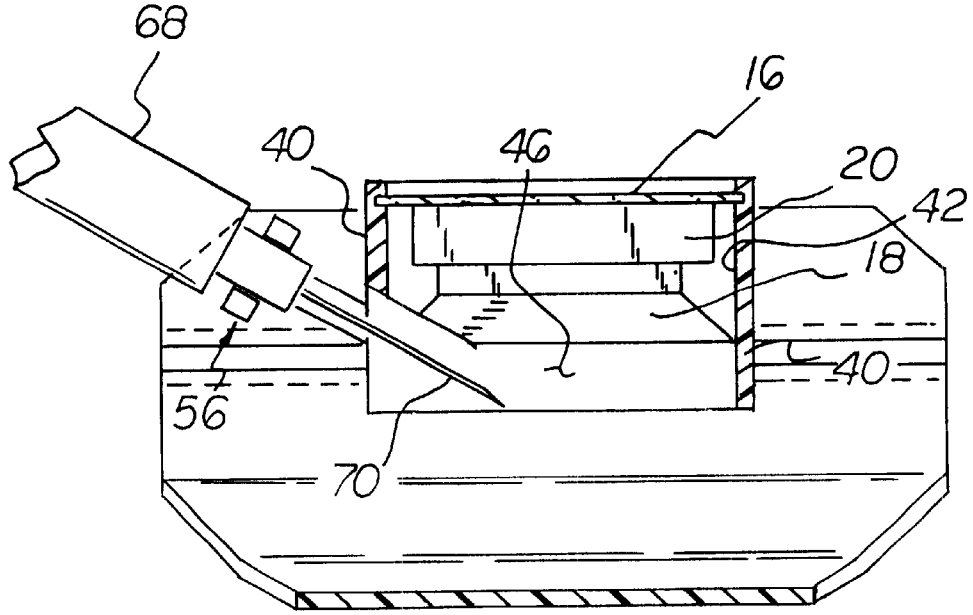
FIG. 4 is a cross sectional view taken along line 4—4 of FIG. 3.
Figure 5:
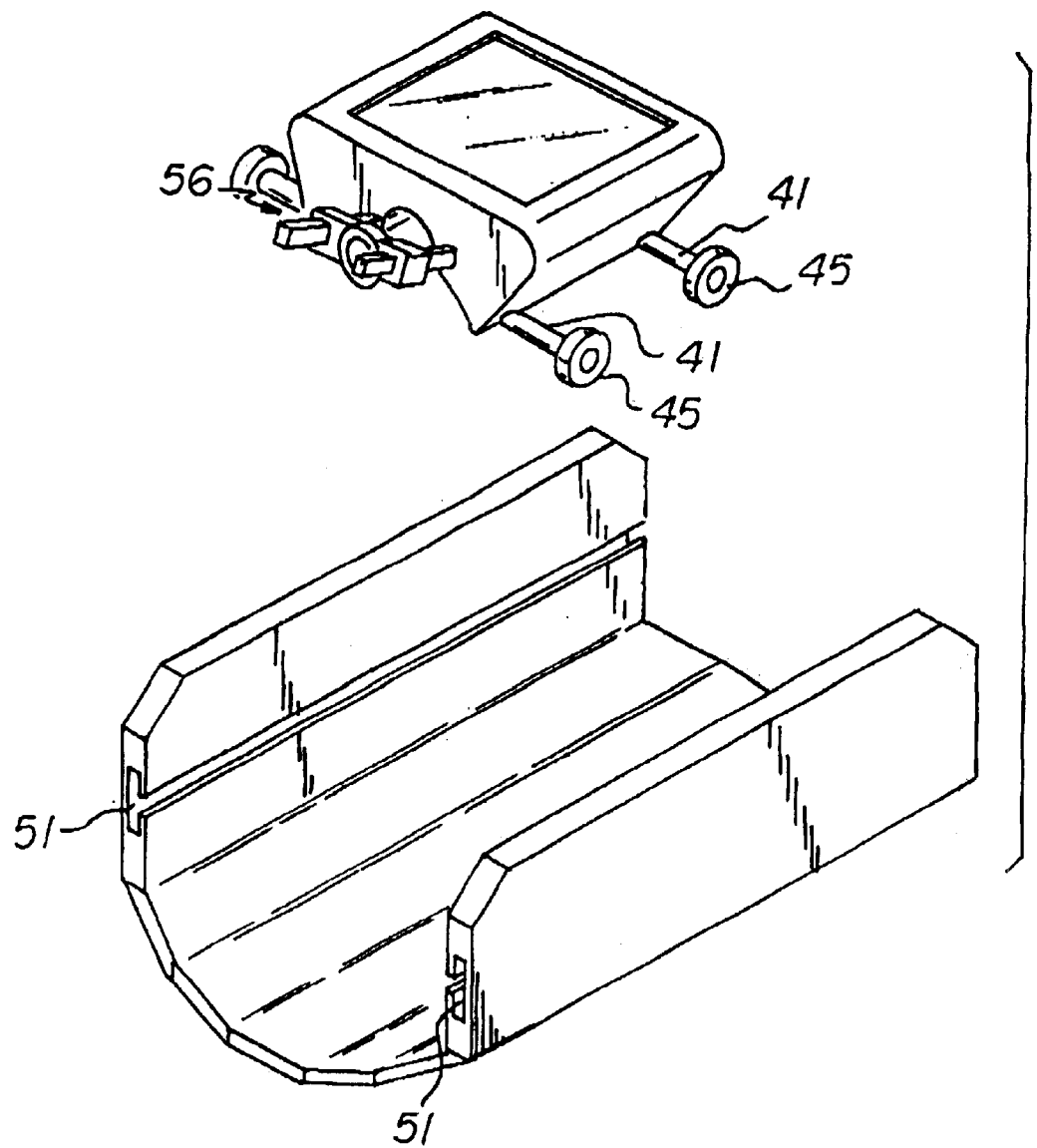
FIG. 5 is a perspective illustration of an alternate embodiment of the invention.

With reference now to the drawings, and in particular to FIG. 1 thereof, the preferred embodiment of the new and improved vein scope and injection system embodying the principles and concepts of the present invention and generally designated by the reference numeral 10 will be described.

The present invention, the vein scope and injection system 10 is comprised of a plurality of components. Such components in their broadest context include a monitor assembly, a support assembly, and a needle handling assembly. Such components are individually configured and correlated with respect to each other so as to attain the desired objective.

First provided is a monitor assembly 14. The monitor assembly includes an image viewing surface formed as a screen 16 in an upper plane. The monitor assembly also includes an image receiving surface formed as a camera 18 in a lower plane parallel with and beneath the upper plane. The monitor assembly also includes electronic components 20 capable of producing an enlarged image upon the viewing screen of an area beneath the camera. The viewing screen is in a rectangular configuration with an upper edge 22 and a lower edge 24 and two parallel sided edges 26 there between. The monitor assembly is formed with a first thickness.

A support assembly 30 is next provided. The support assembly includes a bracket portion 32 and an arm receiving portion 34. The bracket portion is in a rectangular configuration with an upper edge 36 and a lower edge 38 and two parallel side edges 40 there between to thereby form an upper surface and a lower surface. The bracket portion has a central opening 42 located centrally with respect to the screen. The bracket portion and opening form an enclosure for the receipt and secure containment of the monitor assembly within the opening. The bracket portion further has a plurality of axles 41 coupled horizontally adjacent to the image receiving surface. The axles have a first end 43 and a second end 44 with the first end being coupled to the bracket portion and the second end being coupled to a roller 45. These rollers have a central aperture 47 to receive the axle. The support assembly has a second thickness which is less than the first thickness to thereby form a chamber 46 between the edges of the bracket portion and beneath the camera.

The arm receiving portion is of a generally U-shaped trough having an interior surface 48, a pair vertical side walls 49 and a generally semicircular base region 50, thereby defining a region to receive an arm. The vertical side walls each have a horizontal track 51 wherein a recess is nearly covered by an upper lip and lower lip. Together the roller and axle combination fit within the horizontal track of the arm receiver to allow the placement of the arm of a patient in a plane generally parallel to the plane of the camera.

There are three buttons utilized by the present invention and positioned on the top face of the bracket portion. These buttons control the on, off function as well as enlarge and reduce functions.

As shown in FIGS. 1–4, the portion of the support assembly opposite from the monitor also known as the receiver portion is shown as a one piece construction. Such one piece construction could well be fabricated of two pieces, separable and adjustable as by straps with Velcro pile type fasteners and/or elastic for accommodating arms or legs of a variety of sizes.

Next provided is a needle handling assembly 56. The needle handling assembly includes spaced parallel guide rails 58 coupled to the bracket portion adjacent to the lower face and extending away from the bracket portion. The needle handling assembly also includes a slide member 60 with laterally spaced apertures 62 for being slidably received on the rails and with a central aperture 64.

Lastly, a syringe 68 is removably positioned within the central aperture of the slide member. The syringe has a needle 70 extending into the chamber so that the tip of the needle is located within the chamber to allow the movement of the syringe and needle and slide member along the rails for advancement of the needle toward and into a vein during the enlarged viewing of the needle and an appropriate vein of a patient. In this manner precise viewing and venous access is facilitated during operation and use.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A vein scope and injection system for safely and efficiently locating veins to thereby provide precise venous access comprising, in combination:
    a monitor assembly including an image viewing surface formed as a screen in an upper plane and an image receiving surface formed as a camera in a lower plane parallel with and beneath the upper plane, the monitor assembly also including electronic components capable of producing an enlarged image upon the viewing screen of an area beneath the camera, the viewing screen being of a rectangular configuration with an upper edge and a lower edge and two parallel sided edges there between, the monitor assembly being formed with a first thickness;
    a support assembly including a bracket portion and an arm receiving portion, the bracket portion being in a rectangular configuration with an upper edge and a lower edge and two parallel side edges there between to thereby form an upper surface and a lower surface, the bracket portion having a central opening located centrally with respect to the screen, the bracket and opening forming an enclosure for the receipt and secure containment of the monitor assembly within the opening, the bracket assembly further having a plurality of axles coupled horizontally adjacent to the image receiving surface, the axles having a first end and a second end with the first end being coupled to the bracket portion and the second end being coupled to a roller wherein the rollers having a central aperture to receive the axle, the support assembly having a second thickness which is greater than the first thickness to thereby form a chamber between the edges of the bracket portion and beneath the camera, the arm receiving portion being of a generally U-shaped trough having an interior surface, a pair vertical side walls and a generally semicircular base region, thereby defining a region to receive an arm, the vertical side walls each having a horizontal track wherein a recess is nearly covered by an upper lip and lower lip, allowing the roller and axle combination to fit within the horizontal track of the arm receiver thereby allowing the placement of the arm of a patient in a plane generally parallel to the plane of the camera and also allowing movement of the monitor and support assembly relative to the arm receiving portion and arm;
    a needle handling assembly including spaced parallel guide rails coupled to the bracket portion adjacent to the lower face and extending away from the bracket portion, the needle handling assembly also including a slide member with laterally spaced apertures for being slidably received on the rails and with a central aperture; and
    a syringe removably positioned within the central aperture of the slide member, the syringe having a needle extending into the chamber so that the tip of the needle is located within the chamber to allow the movement of the syringe and needle and slide member along the rails for advancement of the needle toward and into a vein during the enlarged viewing of the needle and an appropriate vein of a patient to thereby provide for the precise viewing and venous access during operation and use.

2. A vein scope comprising:
    a monitor assembly including an image viewing surface and an image receiving surface, the monitor assembly being formed with a first thickness;
    a support assembly including a bracket portion and an arm receiving portion, the bracket portion having a central opening forming an enclosure for the receipt and secure containment of the monitor assembly;
    a needle handling assembly including spaced parallel guide rails coupled to the bracket portion, the needle handling assembly also including a slide member with laterally spaced apertures for being slidably received on the rails and with a central aperture.

3. The system as set forth in claim 2 and further including the bracket assembly having a plurality of axles coupled horizontally adjacent to the image receiving surface, the axles having a first end and a second end with the first end being coupled to the bracket portion and the second end being coupled to a roller wherein the rollers having a central aperture to receive the axle, the support assembly having a second thickness which is less than the first thickness to thereby form a chamber between the edges of the bracket portion and beneath the camera, the arm receiving portion being of a generally U-shaped trough having an interior surface, a pair vertical side walls and a generally semicircular base region, thereby defining a region to receive an arm, the vertical side walls each having a horizontal track wherein a recess is nearly covered by an upper lip and lower lip, allowing the roller and axle combination to fit within the horizontal track of the arm receiver thereby allowing the placement of the arm of a patient in a plane generally parallel to the plane of the camera.

4. The system as set forth in claim 2 and further including a syringe removably positioned within the central aperture of the slide member, the syringe having a needle extending into the chamber so that the tip of the needle is located within the chamber to allow the movement of the syringe and needle and slide member along the rails for advancement of the needle toward and into a vein during the enlarged viewing of the needle and an appropriate vein of a patient to thereby provide for the precise viewing and venous access during operation and use.

5. The system as set forth in claim 2 and further including a strap for coupling the monitor assembly and support assembly to a patient's arm.

6. The system as set forth in claim 2 wherein the monitor assembly includes a camera and a screen.

* * * * *